US010675524B2

(12) United States Patent
Arguello, Jr.

(10) Patent No.: US 10,675,524 B2
(45) Date of Patent: Jun. 9, 2020

(54) HORSE TRAINING GOGGLE ASSEMBLY

(71) Applicant: Fabio Arguello, Jr., Louisville, KY (US)

(72) Inventor: Fabio Arguello, Jr., Louisville, KY (US)

(*) Notice: Subject to any disclaimer, the term of this patent is extended or adjusted under 35 U.S.C. 154(b) by 25 days.

(21) Appl. No.: 16/176,314

(22) Filed: Oct. 31, 2018

(65) Prior Publication Data
US 2020/0129831 A1  Apr. 30, 2020

(51) Int. Cl.
| A63B 69/04 | (2006.01) |
| G06F 3/14 | (2006.01) |
| H04B 1/3827 | (2015.01) |
| H04N 7/18 | (2006.01) |
| H04N 5/225 | (2006.01) |
| A42B 3/04 | (2006.01) |
| A63B 24/00 | (2006.01) |
| A61B 5/00 | (2006.01) |

(52) U.S. Cl.
CPC .............. *A63B 69/04* (2013.01); *G06F 3/14* (2013.01); *H04B 1/385* (2013.01); *A42B 3/042* (2013.01); *A61B 5/6895* (2013.01); *A61B 2503/10* (2013.01); *A61B 2503/40* (2013.01); *A63B 24/0021* (2013.01); *H04B 2001/3866* (2013.01); *H04B 2001/3872* (2013.01); *H04N 5/2252* (2013.01); *H04N 7/183* (2013.01)

(58) Field of Classification Search
CPC ... A61B 5/1116; A61B 5/7246; A61B 5/1122; A61B 5/1112; A61B 5/6895; A61B 2503/10; A61B 2503/40; A42B 3/042; A63B 24/0021; A63B 69/04; H04N 5/2252; H04N 7/183; H04B 1/385; H04B 2001/3872; H04B 2001/3866; G06F 3/14
See application file for complete search history.

(56) References Cited

U.S. PATENT DOCUMENTS

| 6,085,428 | A | 7/2000 | Casby et al. | |
| 6,736,759 | B1* | 5/2004 | Stubbs | A63B 22/00 482/8 |
| 7,220,220 | B2* | 5/2007 | Stubbs | A63B 22/00 482/72 |
| 8,398,560 | B2* | 3/2013 | Elser | A61B 5/0059 600/534 |
| 8,620,600 | B2 | 12/2013 | Vock | |
| 9,173,596 | B1* | 11/2015 | Berme | G06F 19/3481 |
| 9,389,677 | B2* | 7/2016 | Hobby | H04B 1/385 |
| 9,414,784 | B1* | 8/2016 | Berme | A63B 24/0021 |

(Continued)

*Primary Examiner* — William H McCulloch, Jr.

(57) ABSTRACT

A horse training goggle assembly includes a pair of goggles that may be worn by a jockey riding a horse during race training. The goggles have a frame and a lens that is removably positioned in the frame. A tracking unit is coupled to the goggles and the tracking unit is in electrical communication with a global positioning system (GPS) to identify a physical location of the jockey. Moreover, the tracking unit calculates a speed and direction of the horse during the race training. A display is embedded within the lens and the display is visible to the jockey when the goggles are worn. The display displays indicia in the lens and the display is electrically coupled to the tracking unit to display data relating to the speed and direction of the horse. A communication unit is coupled to the goggles for verbal communication between the jockey and the trainer.

11 Claims, 6 Drawing Sheets

(56) References Cited

U.S. PATENT DOCUMENTS

| | | | |
|---|---|---|---|
| 9,883,085 B2* | 1/2018 | Piednoir | H04N 5/2252 |
| 10,070,677 B2* | 9/2018 | Durham | A42B 3/04 |
| 10,484,652 B2* | 11/2019 | Hobby | A42B 3/042 |
| 2004/0260191 A1* | 12/2004 | Stubbs | A63B 22/00 |
| | | | 600/520 |
| 2007/0117576 A1* | 5/2007 | Huston | G01S 19/42 |
| | | | 455/461 |
| 2013/0215281 A1* | 8/2013 | Hobby | A42B 3/042 |
| | | | 348/207.1 |
| 2014/0002587 A1 | 1/2014 | Aguren | |
| 2014/0240313 A1 | 8/2014 | Varga | |
| 2015/0153571 A1* | 6/2015 | Ballard | G02B 27/0093 |
| | | | 345/8 |
| 2015/0153826 A1* | 6/2015 | Ballard | G06F 21/71 |
| | | | 345/633 |
| 2016/0355126 A1* | 12/2016 | Anderson | A42B 3/0453 |
| 2017/0265556 A1* | 9/2017 | Yang | A42B 3/128 |
| 2018/0194386 A1* | 7/2018 | Stathis | B62C 1/08 |
| 2018/0279709 A1* | 10/2018 | Durham | A42B 3/066 |
| 2019/0053762 A1* | 2/2019 | Saigh | A61B 5/1112 |
| 2019/0054347 A1* | 2/2019 | Saigh | A61B 5/745 |
| 2019/0192053 A1* | 6/2019 | Saigh | G16H 40/67 |
| 2020/0015740 A1* | 1/2020 | Alnofeli | A61B 5/4872 |

* cited by examiner

HORSE TRAINING GOGGLE ASSEMBLY

CROSS-REFERENCE TO RELATED APPLICATIONS

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to horse training goggle assemblies and more particularly pertains to a new horse training goggle assembly for providing real time performance data to a jockey during horse training.

BRIEF SUMMARY OF THE INVENTION

An embodiment of the disclosure meets the needs presented above by generally comprising a pair of goggles that may be worn by a jockey riding a horse during race training. The goggles have a frame and a lens that is removably positioned in the frame. A tracking unit is coupled to the goggles and the tracking unit is in electrical communication with a global positioning system (GPS) to identify a physical location of the jockey. Moreover, the tracking unit calculates a speed and direction of the horse during the race training. A display is embedded within the lens and the display is visible to the jockey when the goggles are worn. The display displays indicia in the lens and the display is electrically coupled to the tracking unit to display data relating to the speed and direction of the horse. A communication unit is coupled to the goggles for verbal communication between the jockey and the trainer.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
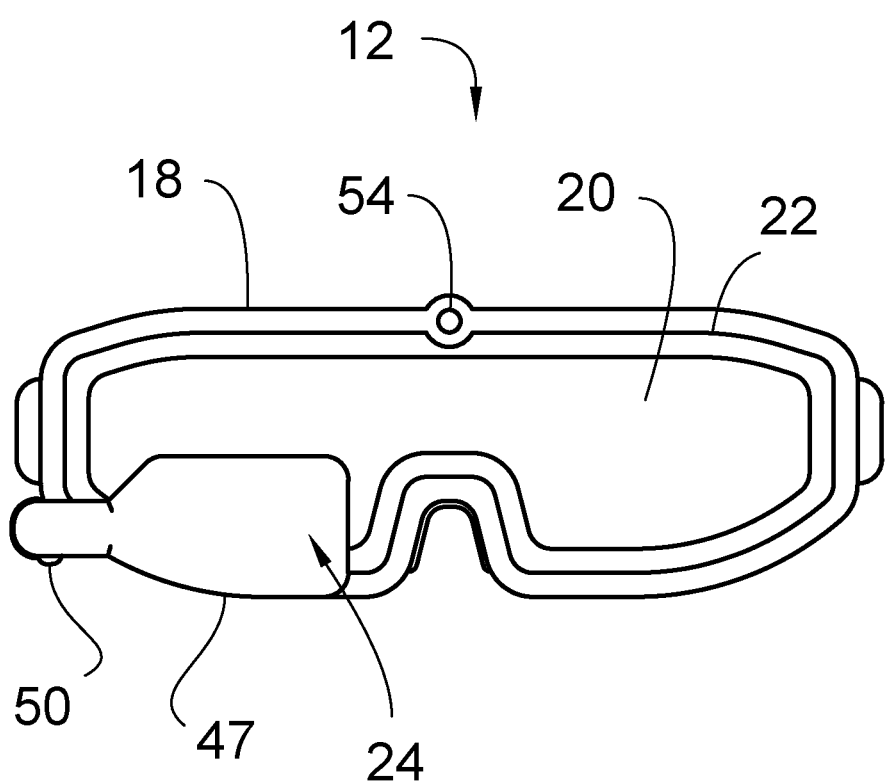
FIG. 1 is a front view of a horse training goggle assembly according to an embodiment of the disclosure.
Figure 2:
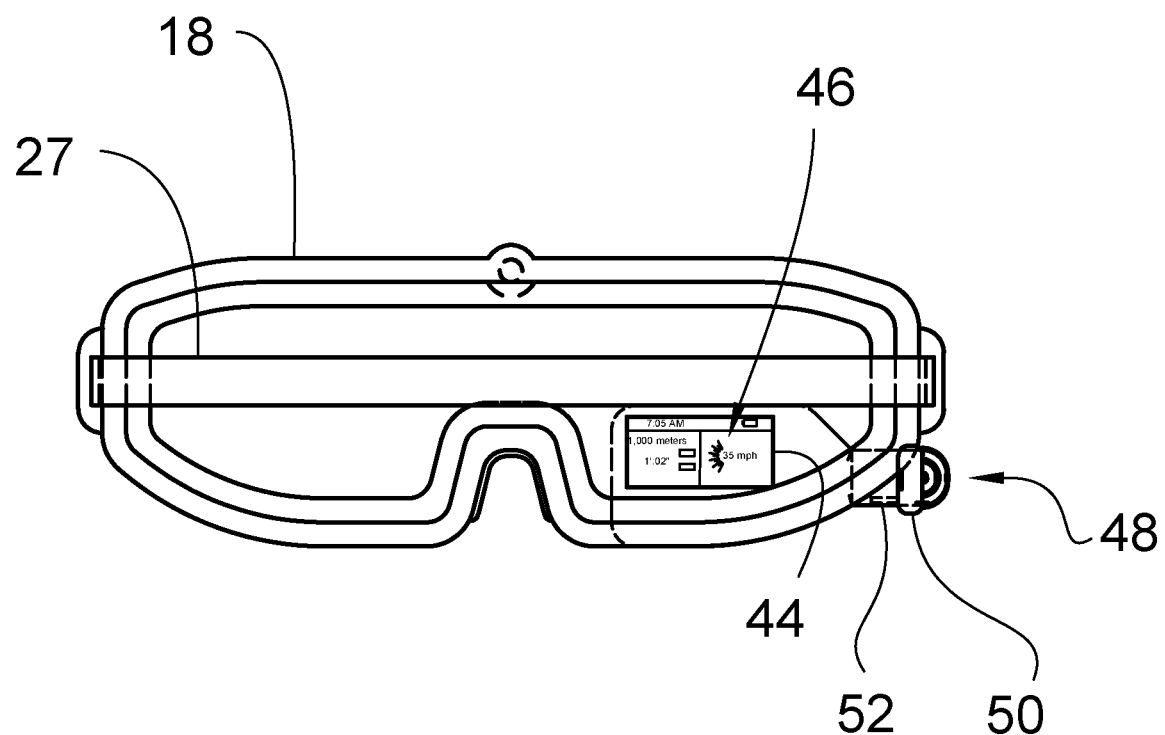
FIG. 2 is a back view of an embodiment of the disclosure.
Figure 3:
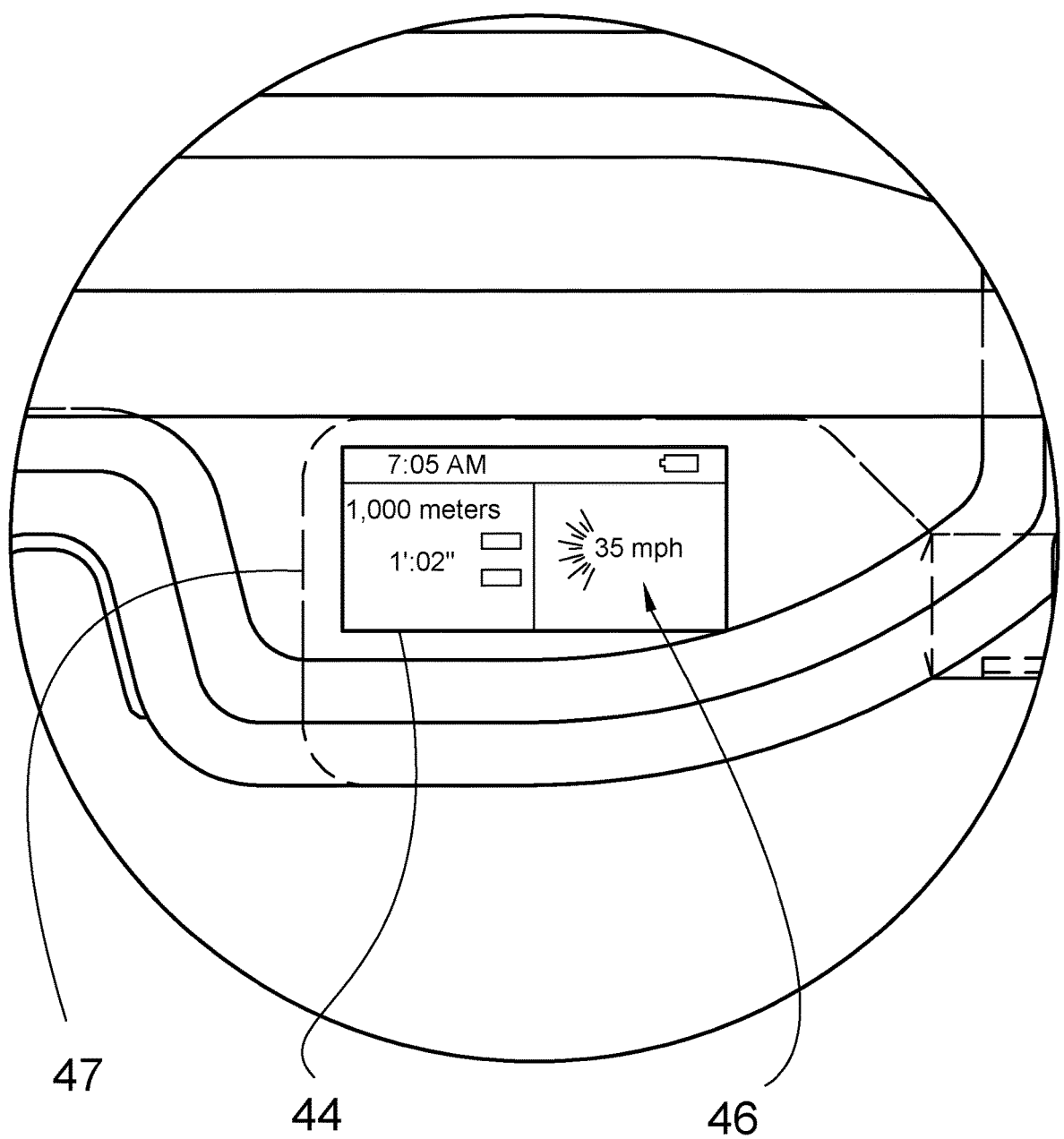
FIG. 3 is a perspective view of a display of an embodiment of the disclosure.
Figure 4:
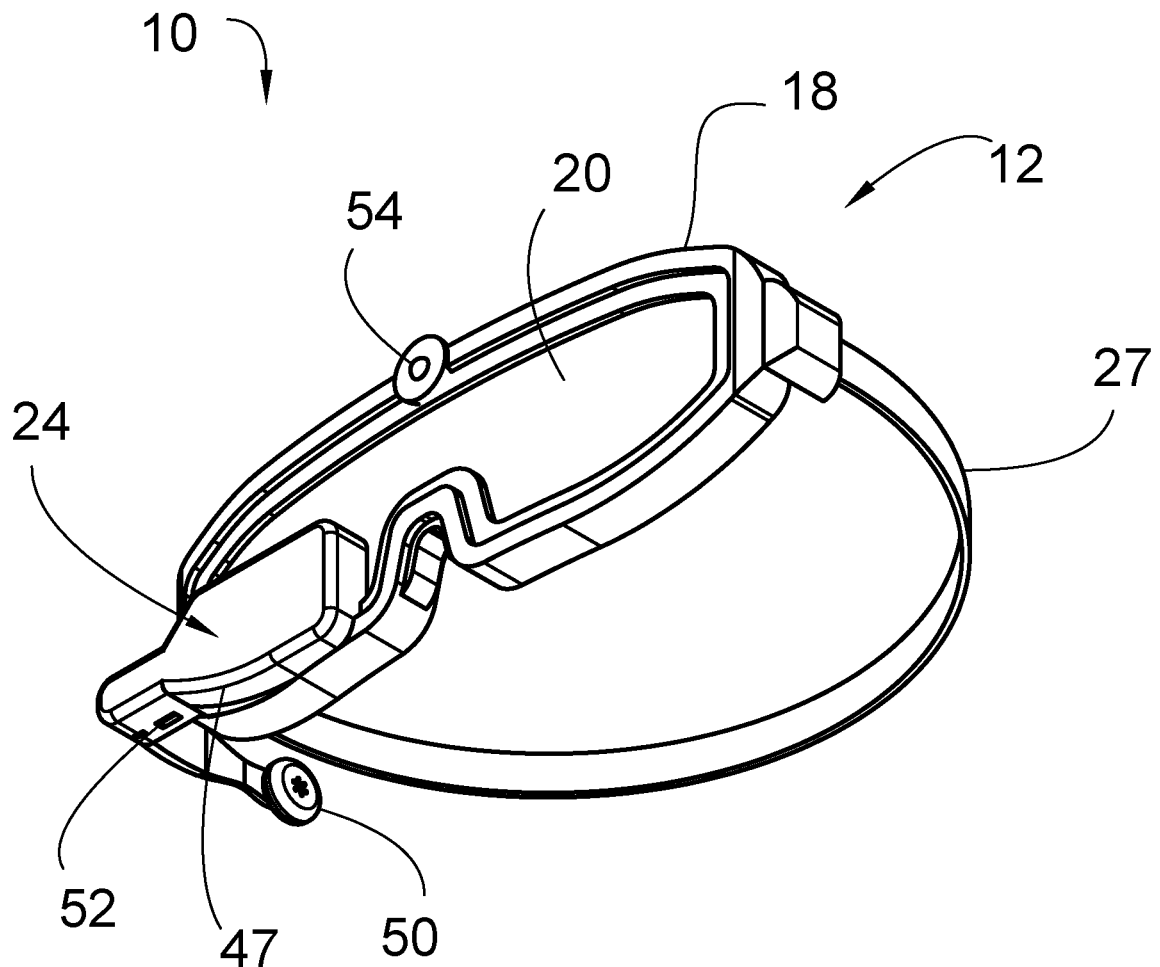
FIG. 4 is a front perspective view of an embodiment of the disclosure.
Figure 5:
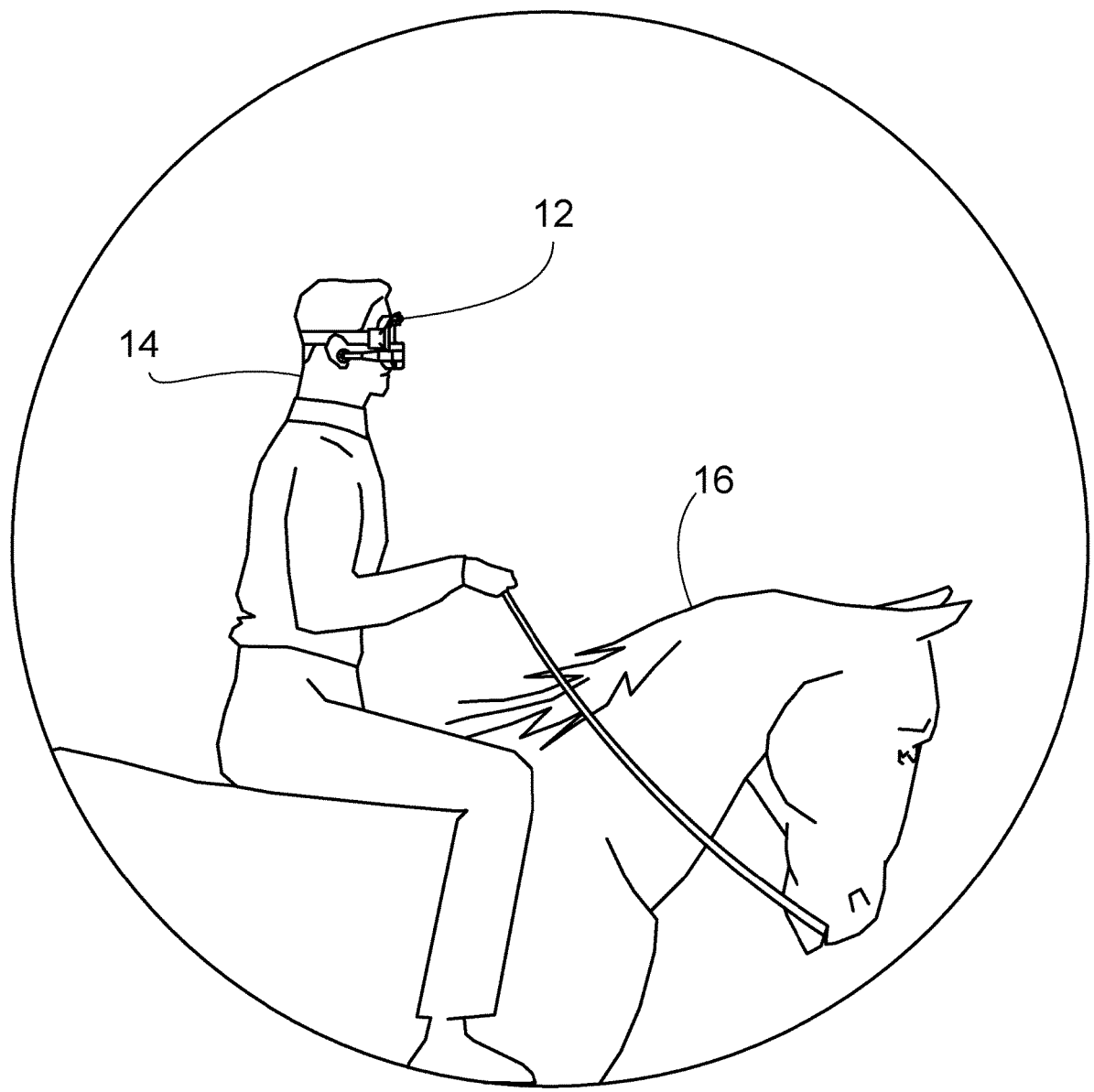
FIG. 5 is a perspective in-use view of an embodiment of the disclosure.
Figure 6:
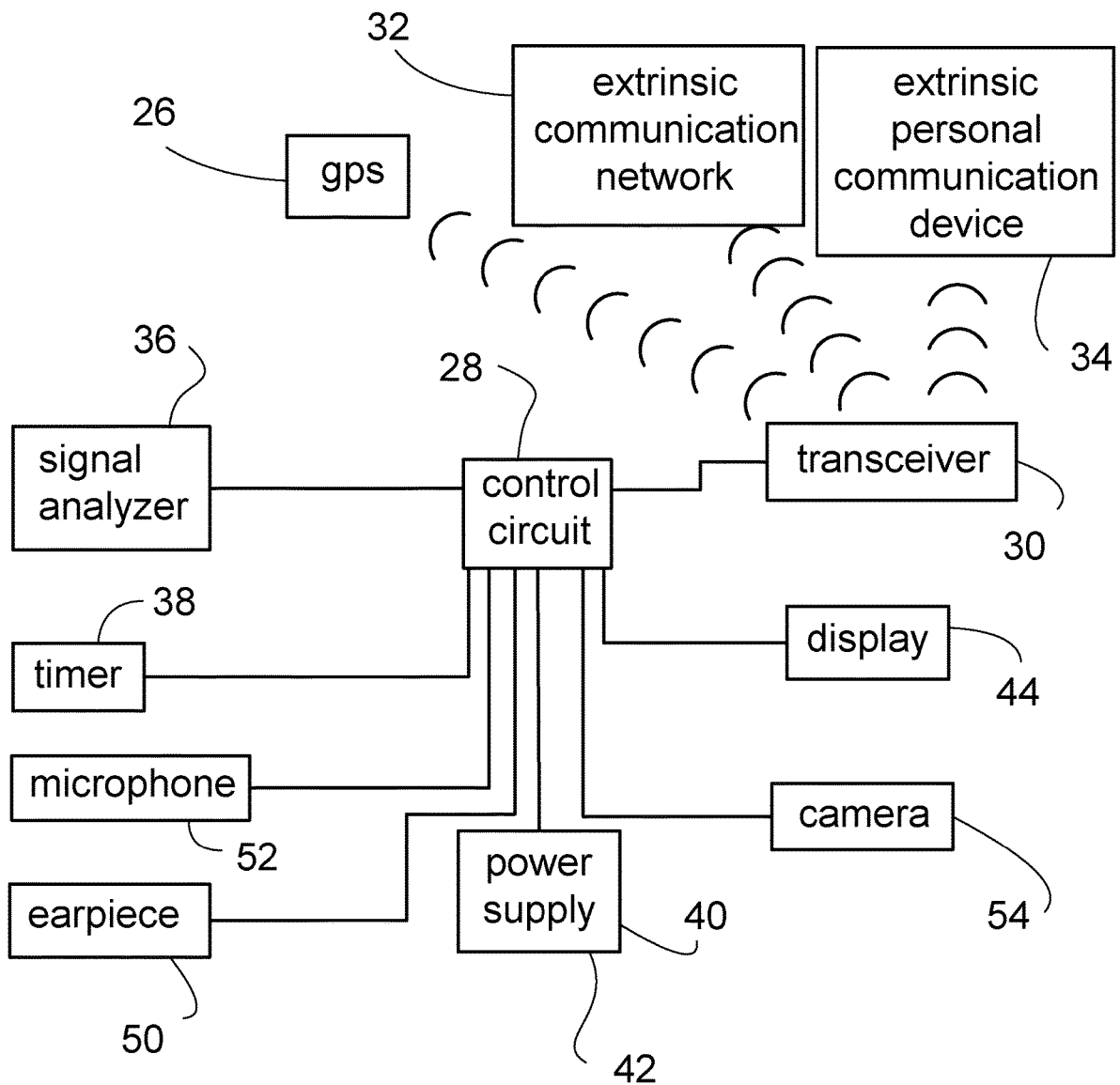
FIG. 6 is a schematic view of an embodiment of the disclosure.

With reference now to the drawings, and in particular to FIGS. 1 through 6 thereof, a new horse training goggle assembly embodying the principles and concepts of an embodiment of the disclosure and generally designated by the reference numeral 10 will be described.

As best illustrated in FIGS. 1 through 6, the horse training goggle assembly 10 generally comprises a pair of goggles 12 that may be worn by a jockey 14 riding a horse 16 during race training. The goggles 12 include a frame 18 and a lens 20 that is removably positioned in the frame 18. The frame 18 has a front side 22 and the goggles 12 may be horse riding goggles of any conventional design. The lens 20 may be a polarized, fog free lens that additionally provides UV protection. The lens 20 may additionally have a scratch resistant coating and meet ANSIZ87.1-2015 safety certification. A tracking unit 24 is coupled to the goggles 12 and the tracking unit 24 is in electrical communication with a global positioning system (GPS) 26. In this way the tracking unit 24 identifies a physical location of the jockey 14 and the tracking unit 24 calculates a speed and direction of the horse 16 during the race training. An elastic strap 27 is coupled to the frame 18 and the elastic strap 27 is capable of being wrapped around a jockey helmet.

The tracking unit 24 comprises a control circuit 28 that is coupled to the frame 18 and a transceiver 30 that is coupled to the frame 18. The transceiver 30 is electrically coupled to the control circuit 28 and the transceiver 30 is in wireless communication with the GPS 26. The transceiver 30 is additionally in wireless communication with an extrinsic communication network 32, such as the internet, or the like, via a wifi portal or a cellular phone network. Thus, the transceiver 30 may be placed in communication with an extrinsic personal communication device 34, such as a smart phone or the like, thereby facilitating a trainer to communicate with the jockey 14. Moreover, the transceiver 30 may receive incoming phone calls from the extrinsic communication network 32 in the convention of a cell phone. The transceiver 30 may be a radio frequency transceiver 30 or the like and the transceiver 30 may employ a WPAN signal and Bluetooth communication protocols.

A signal analyzer 36 is coupled to the frame 18 and the signal analyzer 36 is electrically coupled the control circuit 28. The signal analyzer 36 receives the location data from the GPS 26 to calculate a speed and direction of the horse 16 during race training. The signal analyzer 36 may be an electronic signal analyzer that is capable of deriving all aspects of the horse's motion from the GPS 26 during race training. A timer 38 is coupled to the frame 18 and the timer 38 is electrically coupled to the control circuit 28. The timer 38 calculates an elapsed time of the horse 16 during the race training and the timer 38 may comprise a digital timer or the like.

A power supply 40 is coupled to the frame 18 and the power supply 40 is electrically coupled to the control circuit 28. The power supply 40 comprises at least one battery 42. Moreover, the at least one battery 42 may be a rechargeable battery and a charge port may be coupled to the goggles 12 for charging the at least one battery 42. A display 44 is coupled to the goggle 12 such that the display 44 is visible to the jockey 14 when the goggles 12 are worn. The display 44 displays indicia 46 and the display 44 is electrically coupled to the control circuit 28. Moreover, the display 44 displays indicia 46 relating to data received from the signal analyzer 36. In this way the data is communicated to the jockey 14 in real time during the race training.

The indicia 46 may include a distance the horse has travelled in pre-selected units of measure, such as meters or furlongs. The indicia 46 further includes split times, elapsed times and other times relating to the horse's performance during race training. The indicia 46 further include the speed at which the horse is currently traveling. The display 44 includes a housing 47 that is mounted on the front side 22 of the frame 18 and aligned with the lens 20. The tracking unit 24 may be positioned in the housing or the tracking unit 24 may be embedded within the frame 18 of the goggles 12.

A communication unit 48 is coupled to the goggles 12 and the communication unit 48 is positioned in the jockey's ear when the goggles 12 are worn. The communication unit 48 is in wireless communication with the extrinsic personal communication device 34 to facilitate communication between the jockey 14 and the trainer. The communication unit 48 comprises an earpiece 50 that is coupled to and extends downwardly and rearwardly from the frame 18. The earpiece 50 is positioned in the jockey 14's ear when the goggles 12 are worn and the earpiece 50 is electrically coupled to the control circuit 28. Thus, the earpiece 50 emits speech from the trainer that was received from the transceiver 30. The earpiece 50 may include an electronic speaker or any other electronic means of communicating audible sounds.

A microphone 52 is coupled to the frame 18 for detecting audible sound. The microphone 52 is electrically coupled to the control circuit 28 to transmit speech from the jockey 14 to the transceiver 30. Moreover, the control circuit 28 responds to a plurality of pre-determined voice commands. In this way the tracking unit 24 can be controlled with voice commands thereby facilitating hands free control for the jockey. The microphone 52 may be an electronic microphone or the like.

A camera 54 is coupled to the front side 22 of the goggles 12 to capture images when the goggles are worn and the camera 54 is electrically coupled to the control circuit 28. The camera 54 may be an electronic camera 54 or the like and the transceiver 30 may stream the images to an electronic storage unit, such as a computer hard drive or the like, for storing the images. Additionally, the electronic storage unit may store performance data relating to the horse's race times and speed for subsequent analysis.

In use, the goggles 12 are worn when the jockey 14 is riding the horse 16 during race training. The transceiver 30 communicates with the GPS 26 to establish the physical location of the jockey 14 and the signal analyzer 36 determines the speed and direction of the horse 16. The speed and direction, along with other performance parameters of the horse's motion, are continuously displayed in the display 46 so the jockey 14 has real time data. The timer 38 tracks elapsed time for laps and other milestones in horse race training. Moreover, the jockey 14 and the trainer are in constant communication via the earpiece 50 and the microphone 52 when the jockey 14 is riding the horse 16. The transceiver 30 continuously broadcasts the speed, direction and other performance parameters for storage and subsequent analysis on a computer, smart phone or other electronic storage device.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A horse training goggle assembly being configured to monitor speed and elapsed time of a horse during race training, said assembly comprising:
   a pair of goggles being configured to be worn by a jockey riding a horse during race training, said goggles having a frame and a lens being removably positioned in said frame, said frame having a front side;
   a tracking unit being coupled to said goggles, said tracking unit being configured to be in electrical communication with a global positioning system (GPS) thereby facilitating said tracking unit to identify a physical location of the jockey, said tracking unit calculating a speed and direction of the horse during the race training;
   a display being embedded within said lens wherein said display is configured to be visible to the jockey when said goggles are worn, said display displaying indicia in said lens, said display being electrically coupled to said tracking unit such that said display displays data relating to the speed and direction of the horse; and
   a communication unit being coupled to said goggles wherein said communication unit is configured to be positioned in the jockey's ear when said goggles are worn, said communication unit being configured to be in wireless communication with an extrinsic personal communication device thereby facilitating communication between the jockey and the trainer.

2. The assembly according to claim 1, further comprising said tracking unit comprises a control circuit being coupled to said frame.

3. The assembly according to claim 2, further comprising a transceiver being coupled to said frame, said transceiver being electrically coupled to said control circuit, said transceiver being configured to be in wireless communication with the GPS, said transceiver being configured to be in wireless communication with an extrinsic communication network, said transceiver being configured to be in wireless communication with the extrinsic personal communication device thereby facilitating a trainer to communicate with the jockey.

4. The assembly according to claim 3, further comprising a signal analyzer being coupled to said frame, said signal analyzer being electrically coupled said control circuit such that said signal analyzer receives the location data from the GPS wherein said signal analyzer is configured to calculate a speed of the horse during race training.

5. The assembly according to claim 4, further comprising a timer being coupled to said frame, said timer being electrically coupled to said control circuit, said timer being configured to calculate an elapsed time of the horse during the race training.

6. The assembly according to claim 5, further comprising said display being electrically coupled to said control circuit, said display displaying indicia relating to data received from said signal analyzer wherein said display is configured to communicate the data to the jockey in real time during the race training.

7. The assembly according to claim 3, wherein said communication unit comprises an earpiece being coupled to said frame wherein said earpiece is configured to be positioned in the jockey's ear, said earpiece being electrically coupled to said control circuit wherein said earpiece is configured to emit speech from the trainer received from said transceiver.

8. The assembly according to claim 7, further comprising a microphone being coupled to said frame wherein said microphone is configured to detect audible sound, said microphone being electrically coupled to said control circuit wherein said microphone is configured to transmit speech from the jockey to said transceiver.

9. The assembly according to claim 2, further comprising a power supply being coupled to said frame, said power supply being electrically coupled to said control circuit, said power supply comprising at least one battery.

10. The assembly according to claim 2, further comprising a camera being coupled to said goggles wherein said camera is configured to capture images, said camera being electrically coupled to said control circuit.

11. A horse training goggle assembly being configured to monitor speed and elapsed time of a horse during race training, said assembly comprising:
a pair of goggles being configured to be worn by a jockey riding a horse during race training, said goggles having a frame and a lens being removably positioned in said frame, said frame having a front side;
a tracking unit being coupled to said goggles, said tracking unit being configured to be in electrical communication with a global positioning system (GPS) thereby facilitating said tracking unit to identify a physical location of the jockey, said tracking unit calculating a speed and direction of the horse during the race training, said tracking unit comprising:
a control circuit being coupled to said frame; and
a transceiver being coupled to said frame, said transceiver being electrically coupled to said control circuit, said transceiver being configured to be in wireless communication with the GPS, said transceiver being configured to be in wireless communication with an extrinsic communication network, said transceiver being configured to be in wireless communication with an extrinsic personal communication device thereby facilitating a trainer to communicate with the jockey;
a signal analyzer being coupled to said frame, said signal analyzer being electrically coupled said control circuit such that said signal analyzer receives the location data from the GPS wherein said signal analyzer is configured to calculate a speed of the horse during race training;
a timer being coupled to said frame, said timer being electrically coupled to said control circuit, said timer being configured to calculate an elapsed time of the horse during the race training; and
a power supply being coupled to said frame, said power supply being electrically coupled to said control circuit, said power supply comprising at least one battery;
a display being embedded within said lens wherein said display is configured to be visible to the jockey when said goggles are worn, said display displaying indicia in said lens, said display being electrically coupled to said tracking unit such that said display displays data relating to the speed and direction of the horse during the race training, said display being electrically coupled to said control circuit, said display displaying indicia relating to data received from said signal analyzer wherein said display is configured to communicate the data to the jockey in real time during the race training; and
a communication unit being coupled to said goggles wherein said communication unit is configured to be positioned in the jockey's ear when said goggles are worn, said communication unit being configured to be in wireless communication with the extrinsic personal communication device thereby facilitating communication between the jockey and the trainer, said communication unit comprising:
an earpiece being coupled to said frame wherein said earpiece is configured to be positioned in the jockey's ear, said earpiece being electrically coupled to said control circuit wherein said earpiece is configured to emit speech from the trainer received from said transceiver; and
a microphone being coupled to said frame wherein said microphone is configured to detect audible sound, said microphone being electrically coupled to said control circuit wherein said microphone is configured to transmit speech from the jockey to said transceiver; and
a camera being coupled to said goggles wherein said camera is configured to capture images, said camera being electrically coupled to said control circuit.

* * * * *